United States Patent [19]

Gongora et al.

[11] Patent Number: 4,699,736

[45] Date of Patent: Oct. 13, 1987

[54] MANUFACTURE OF ALKANE SULPHONYL CHLORIDES

[75] Inventors: Henri Gongora, Billere; Jacques Tournier-Lasserve, Pau, both of France

[73] Assignee: Societe Nationale Elf Aquitaine (Production), France

[21] Appl. No.: 429,448

[22] Filed: Sep. 30, 1982

Related U.S. Application Data

[63] Continuation of Ser. No. 263,133, May 13, 1981.

[30] Foreign Application Priority Data

May 16, 1980 [FR] France ................. 80 10993

[51] Int. Cl.$^4$ ........................... C07C 143/70
[52] U.S. Cl. ............................ 260/543 R
[58] Field of Search ....................... 260/543 R

[56] References Cited

U.S. PATENT DOCUMENTS

| | | | |
|---|---|---|---|
| 3,248,423 | 4/1966 | Stratton | 260/543 R |
| 3,626,004 | 12/1971 | Guertin | 260/543 R |
| 3,993,692 | 11/1976 | Giolito et al. | 260/543 R |
| 4,280,966 | 7/1981 | Hubenett | 260/543 R |

FOREIGN PATENT DOCUMENTS 1811768 11/1968 Fed. Rep. of Germany.

*Primary Examiner*—Paul J. Killos
*Assistant Examiner*—L. Hendriksen
*Attorney, Agent, or Firm*—Ostrolenk, Faber, Gerb & Soffen

[57] ABSTRACT

Continuous manufacture of an alkane sulphonyl chloride by the action of chlorine on the dialkyl disulphide corresponding to the alkane, in the presence of water or an aqueous hydrochloric acid solution.

Firstly, a fine emulsion of the dialkyl disulphide is prepared with water or with an aqueous hydrochloric acid solution, after which the emulsion is treated with chlorine under constant agitation.

Preferably, separation of the alkane sulphonyl chloride formed is effected in two different zones, the second of which operates under reduced pressure.

15 Claims, 1 Drawing Figure

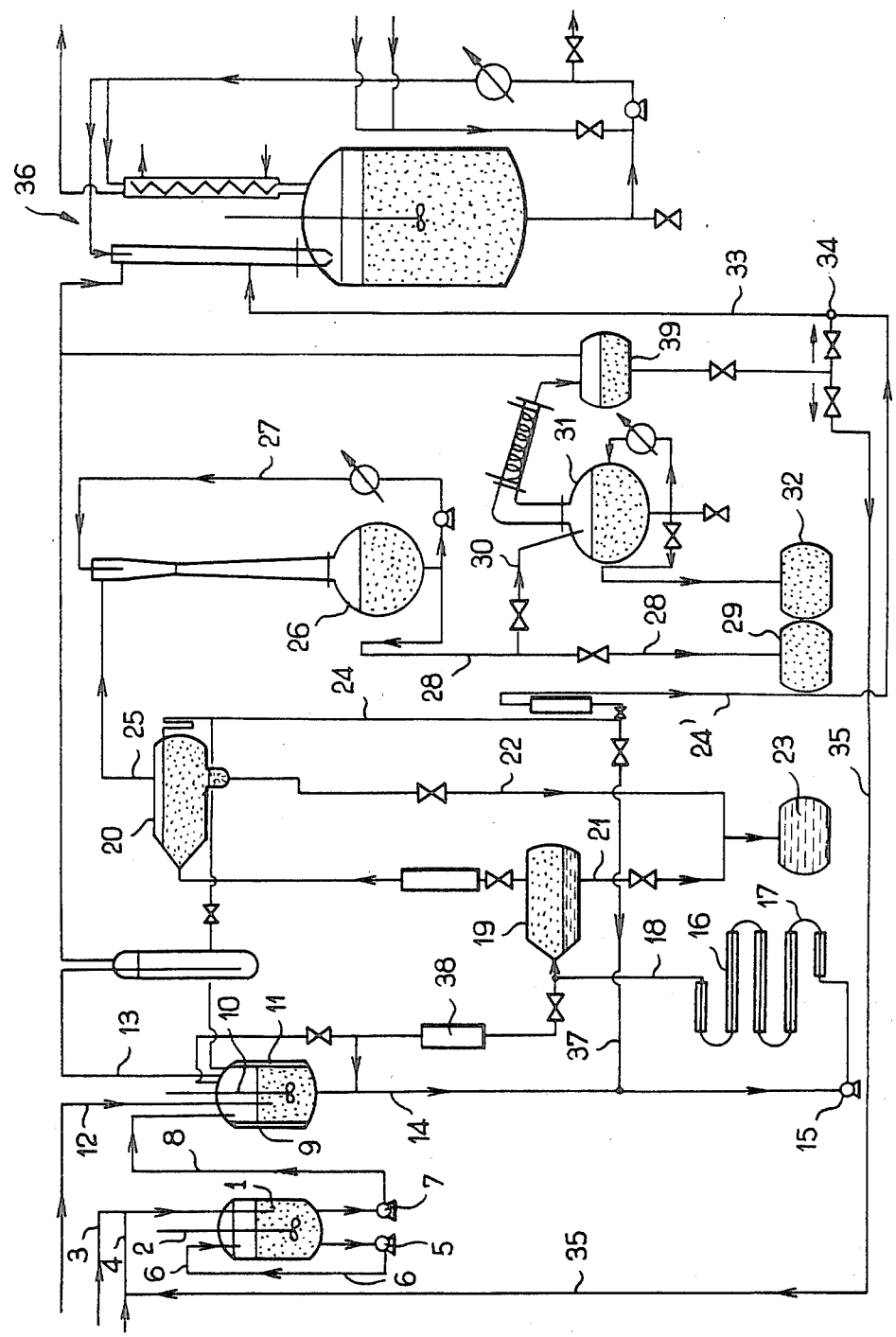

MANUFACTURE OF ALKANE SULPHONYL CHLORIDES

This is a continuation of application Ser. No. 263,133, filed May 13, 1981.

The present invention relates to a novel process for the manufacture of alkane sulphonyl chlorides, which are liquids at ordinary temperature, and of the corresponding acids.

Alkane sulphonyl chlorides, particularly methane sulphonyl chloride, $ClCH_3SO_2$, are interesting industrial products. They have various applications, particularly as intermediates in the production of corticosteroids, photographic products, pharmaceuticals, dyes and other chemical compounds. Thus, their preparation has been studied for a long time. In 1938, Douglass and Johnson (J. Amer. Chem. Soc. 1938, No. 60, p 1486-89) described the reaction of organic disulphides and mercaptans with chlorine in aqueous hydrochloric acid, giving aryl and aliphatic sulphonyl chlorides. They prepared in this way benzene sulphonyl, ethane sulphonyl, n-pentane sulphonyl and n-butane sulphonyl chlorides. This reaction has later been applied industrially, particularly for the manufacture of methane sulphonyl chloride. The process generally adopted comprises contacting the organic disulphide or mercaptan with chlorine and with a concentrated aqueous solution of HCl, in the bottom of a reactor. The sulphonyl formed is then separated from the reaction mixture. The principle of the process has thus been known for a long time, industrial users seeking to render it as economical as possible, principally by varying the mode of circulation of the reactant liquids. This is the object particularly of U.S. Pat. No. 3,993,692, according to which the mercaptan, $CH_3SH$, chlorine and a concentrated solution of HCl are continuously fed, via three separate inlets, into the bottom of a reactor provided with transverse baffles; between the latter rotate the blades of an agitator which serves to mix well the reactants introduced in a pulverized state, in order to avoid the formation of large drops. By these means, it is attempted to render the reaction complete and rapid. For the same purpose, French Pat. No. 1,598,279 recommends the separate introduction of a disulphide or a mercaptan and chlorine into a hydrochloric acid solution present in the bottom of a reactor, in such a manner as to produce a violent evolution of gaseous HCl upwardly and thus cause a turbulence in the reaction zone.

Although these prior art methods allow the reaction to be carried out rapidly, they involve disadvantages and technical difficulties and, particularly so far as concerns the aforementioned French patent, do not always allow the formation of "chimneys" of the HCl currents to be avoided, which are prejudicial to regularity of operation and to good yields.

The present invention provides an improvement which renders possible obtaining a completely homogeneous reaction medium, which ensures a very initmate contact between the reactant substances. Due to this improvement, manufacture takes place smoothly and can be carried out in simple apparatus, without baffles or turbulence, but by means of rotating machines, the mixing obtained from which leads to excellent yields.

The process according to the invention is characterized in that the reaction zone is continuously supplied on the one hand with a previously-stabilized emulsion formed from the organic disulphide in water and/or an aqueous solution of HCl and on the other hand with chlorine. The reaction medium is continually mechanically agitated and is drawn off in order to be conducted rapidly through a cooling system.

Passage through the latter system takes place at such a speed that there is no possibility of separation into two layers and this permits the necessary thermal transfer.

Moreover, a part of the liquid is directed into a separation zone where the alkane sulphonyl chloride is recovered, while the aqueous hydrochloric phase passes on for recovery of the hydrochloric solution and gaseous HCl.

According to a preferred feature of the invention, at least two successive separating zones are utilized, the second receiving the aqueous phase from the first. The sulphonyl entrained by this phase is separated in the second zone and is re-united with that recovered from the first separating zone.

In contrast to the practice according to the prior art, the preferred form of the invention comprises circulation of the reaction liquid from top to bottom through the reaction zone and not in the ascending direction. This is the more advantageous as the alkane sulphonyl chloride is the more dense.

The principal condition of the invention, namely previous formation of an emulsion of the organic disulphide with water and/or an aqueous hydrochloric solution, can be carried out by any known means, but the droplets of the emulsion should be as fine as possible and in any case have a diameter below 100 microns and, preferably, not above 20 microns. Emulsions having droplets of 0.1 to 10 microns are particularly suitable. These emulsions can be of the type where the disulphide is in the aqueous phase, where the aqueous phase is in the disulphide or the two together. When the compound is dimethyl disulphide, having a density at 15° of 1.057, which thus equals that of an aqueous solution of 125 g HCl/l and approximates that of water, and the surface tension is thus low with respect to the hydrochloric solution and to water, emulsification can be readily effected by mechanical agitation and/or rapid circulation in a closed cycle, in an apparatus of the static mixer type for example.

According to this latter particular feature of the invention, it is possible to emulsify the disulphide intimately with the hydrochloric solution and/or water, irrespective of the relative densities of these liquids. A complementary means consists in circulating a large proportion of the reaction medium continuously between the reaction zone and the settling zone. By way of example, this result can be obtained by circulating the reaction liquid in a circuit including an exchanger, such that only 1/6 to ⅓ is continuously transmitted for separation. Vigorous agitation is thus produced, which prevents any separation into two layers, before the liquid reaches the settling zone.

However, it can be useful to create a very fine emulsion by the addition of a surfactant. The latter can be selected from any of the known standard surface active agents, particularly cationic or non-ionic, for example quaterniary sulphonium or ammonium salts or polyoxyalkylenes, which are active in a hydrochloric medium. It is always necessary to take account of the chemical nature of the agent with regard to the reactant materials of the process. Thus, surfactants destroyable by chlorine are recommendable, because they permit emulsification of the disulphide/water/HCl mixture before chlorination and gradually disappear during this reaction, which avoids any risk of subsequent emulsification of the alkane sulphonyl chloride produced when about to separate it from the aqueous phase. Such agents are to be found in the quaterniary ammonium and polyoxyalkylene groups. Another solution consists in employing a surfactant mercaptan, for example, a polyethoxymercaptan or dodecyl-mercaptan which, during the reaction, can give intermediate products which do not prevent the sulphonyl from being obtained. If this surfactant remains in the sulphonyl manufactured, it has a much larger molecular weight than the sulphonyl itself and does not affect purification of the latter.

In any event, since it is sufficient to have a very low amount of the surfactant, of the order of 0.001% to 0.1%, addition of this substance has no adverse effect on the purity of the alkane sulphonyl chloride manufactured.

As with known procedures, that of the invention can be carried out at temperatures from about $-10°$ to $+60°$ C., preferably from $0°$ to $20°$ C. and most preferably between $5°$ and $10°$ C. The reaction takes place under atmospheric pressure, but it can be useful to operate under a pressure which can attain several bars, particularly when employing a slight excess of chlorine. The pressures preferred are of the order of 1.1 to 1.5 bars absolute. Although the stoichiometric proportion of $Cl_2$ with respect to the disulphide is suitable, that is to say 5 moles of $Cl_2$ per 1 mole of RSSR, according to the reaction:

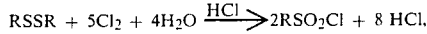

$$RSSR + 5Cl_2 + 4H_2O \xrightarrow{HCl} 2RSO_2Cl + 8 HCl,$$

it can also be useful to utilize a slight excess of $Cl_2$, not exceeding 5%, with respect to this proportion. In contrast, it is recommendable to operate with an excess of water, that is, from 1 to 4 times the quantity of water indicated by the above equation, quantities which are 1.1 to 3 times that amount being particularly suitable, representing 4.4 to 12 moles of $H_2O$ per mole of disulphide.

The preferred concentrations of HCl in the aqueous phase are from 10% to 45% and in particular 25% to 37%.

The apparatus for carrying out the process according to the invention, like the known installations, comprises one or several reactors having an outlet connected to a cooling system and downstream therefrom, a separation device operating by settling. Means are provided for recycling a fraction of the hydrochloric acid recovered at the outlet from the separator. In accordance with the invention, this apparatus is characterized in that an emulsion generator is located upstream of the reactor, the outlet from this emulsifier being connected to the inlet to the reactor. The feed to the emulsifier comprises a tube supplied with the organic disulphide and an inlet for water and/or the aqueous HCl solution derived from a recycled stream for recovery of the HCl.

Preferably, the outlet for the emulsion is constituted by a side-tube at the base of the generator, which is in communication with the top of the reactor.

By way of non-limitative illustration, the single FIGURE diagrammatically represents an apparatus for carrying out the invention.

In this drawing, 1 represents the housing of an emulsifier containing an agitator 2, which can be a turbomixer, for example. The starting materials are introduced into the emulsifier continuously, the disulphide via the inlet 3 and the hydrochloric solution or water via 4. They are vigorously mixed by means of the agitator 2 in order to give a fine emulsion. To enhance the effect of the emulsion, a pump 5 is provided which continuously takes the liquid from the base of the apparatus and directs it via a nozzle 6 into the top of the emulsifier.

A pump 7 transmits the emulsion from 1 at a continuously determined rate through a line 8 into the upper part of a reactor 9, to which chlorine is also fed via an inlet 12. The reactor 9 is provided with a double cooling jacket 11 and an agitator 10.

The reaction having taken place at least to a large extent in the reactor 9, the contents of the latter are maintained at a constant level and are continuously evacuated via a tube 14 by means of a pump 15 and pass into the tubes 17 of a heat-exchanger 16 designed for rapid circulation, preventing separation of the sulphonyl product and favouring thermal exchange. The temperature is maintained at the desired value and as the reaction is completed in the exchanger 16,17, the liquid is conducted via 18 into a first separator 19, the base of which communicates at 21 with a receptacle 23 for the sulphonyl product.

In order to maintain the reaction medium in the state of a homogeneous emulsion which has no tendency to separate into layers in the exchanger 16,17, an abundant recirculation is provided by the shunt 38 upstream of the inlet to the first separator 19. Thus, a relatively small part of the liquid arriving at 18 is introduced into the separator 19. The major part, namely 5/6 to ⅔, is directed via 38 to the line 14 or the inlet to the reactor 9 in order to pass again through the exchanger 16,17, under the effect of the pump 15.

At the top of the separator 19, the upper liquid phase passes up into a second separator 20 where the separation of the sulphonyl is completed. From the base of 20, the product is recovered at 22 in a common receptacle 23. This second separator 20 is under a certain sub-pressure in order to degasify the HCl produced continuously in the aqueous solution and to reduce the acid concentration of the latter. In practice, a suitable sub-pressure is of the order of 10 to 500 millibars and the concentration of the solution, after degasifying the HCl, is about 25% to 35%.

The gas and vapours thus separated in the separator 20 are supplied via the inlet 25 to the top of an ejector-scrubber 26, the absorption water from which is pumped via the inlet 27 and plays the part of a motor fluid. The technical HCl acid thus obtained at 26 is recovered and taken via line 28 into a receiver 29, while a fraction can be derived via 30 and supplied to an evaporator 31 with a view to its purification, the HCl so purified being received in a receptacle 32.

The aqueous phase of reduced concentration in HCl leaving the separator 20 passes through the line 24 in order to be recycled in part through the recirculation loop 38, 14, 15, 16, 17, 18, via 37, to the inlet to the pump 15 and/or the inlet to the reactor 9. The rest of the liquid passes via 24' and 33 to a purge and neutralization installation 36.

In the case where the recovery of methane-sulphonic acid is envisaged, a take-off is provided in the line 24' in order to withdraw some of the solution into a device for the hydrolysis of methane sulphonyl chloride, with a view to making $CH_3SO_3H$.

Reference 36 designates generally a neutralization apparatus for all the gaseous and liquid effluents from various parts of the apparatus.

The non-limitative example which follows shows the operation of a pilot apparatus constructed in accordance with the description given above.

EXAMPLE

Continuous production of methane sulphonyl chloride.

In an emulsifier 1 of stainless steel of 60 liters capacity, a constant input of disulphide, $CH_3SSCH_3$, of 2.5 kg/h, viz. 26.5 moles/h, is effected via 3 and, via 4, a 25% aqueous HCl solution is supplied at a rate representing 5.7 kg/h of water, that is 317 moles $H_2O$/h. The proportion of water with respect to the disulphide is thus 3 times the stoichiometric quantity. Operation takes place at the ambient temperature. The pump 5 supplies 1,000 l/h, which produces a considerable mixing of the liquid mixture, the contents of the emulsifier being recirculated 17 times (1,000:60=16.66). A very fine and stable emulsion is thus obtained, 80% of the droplets of which have a diameter of 1 to 20 microns. Omitting the HCl, the composition of this emulsion by weight is 31.5% $CH_3SSCH_3$ and 68.5% $H_2O$. The reactor 9, of steel coated with glass on the inside, has a capacity of 100 l. The pump 7 supplies the reactor 9 with 8.25 kg/h of emulsion. At the same time, an hourly input of 9.4 to 9.7 kg of gaseous chlorine passes directly into the liquid through the conduit 12 provided with a diffuser. The first of these numbers corresponds to the stoichiometric ratio and the second to an excess of 3%.

The agitator 10 with 3 blades rotates at 150 revs/min. The temperature of the reaction mixture in the reactor 9 is maintained at 7° to 10° C. by circulation of a liquid which enters at −8° C. into the double jacket 11. A pressure of 1.5 bar absolute is maintained in the reactor 9. The tubular exchanger 16,17 of steel coated with glass has a usable capacity of 60 l. It receives via the pump 15 from the reactor 9 an input of 6 to 8 m³/h of the reaction mixture, which it maintains at a temperature of 5°-10° C. A fraction of 1 to 2 m³, namely 1/6 to ⅓ of this amount, passes into the separator 19, the rest constituting the recirculating mass being agitated via 38, 14, 15, 16, 17 and 18, this mass thus arriving partly at the bottom and partly at the top of the reactor 9.

The mixture thus undergoes separation in the two separators 19 and 20 in series which allow the sulphonyl product to flow into the receptacle 23 at the rate of 5.65 to 5.80 kg/h, which corresponds to a yield of 92.5% to 95%.

The hydrochloric acid recovered from the gaseous phase in the separator 20, purified at 31 and recovered at 39 is recycled in part to the emulsifier 1 via the line 35. It thus supplies an aqueous hydrochloric solution for the preparation of the emulsion described above. 2 to 8 kg/h of aqueous liquid from the separator 20 is purged via the lines 24, 24' 33, the remainder being recycled to the reaction vessel.

Conversion of the initial disulphide is practically complete.

The crude product obtained has the average composition:

| | |
|---|---|
| methane sulphonyl chloride | 98 to 98.5% |
| HCl | 1 to 1.5% |
| methane sulphonic acid, approx | 0.5% |
| dimethyl-disulphide | trace |

After distillation, 99.8% methane sulphonyl chloride is recovered containing not more than 0.18% HCl and 100 ppm of disulphide.

The invention also comprises recovery of the methane sulphonic acid, present as a by-product, in the aqueous hydrochloric phase of the process.

We claim:

1. In a continuous process of manufacturing an alkane sulphonyl chloride by the reaction of a dialkyl disulphide, the alkyl of which has the same number of carbon atoms as the alkane sulphonyl chloride to be prepared, with aqueous hydrochloric acid and chlorine, the improvement which comprises
   (a) emulsifying the dialkyl disulphide with hydrochloric acid containing water to an emulsion the droplets of which do not exceed 100 microns in diameter;
   (b) continuously feeding the emulsion obtained into a reaction zone and simultaneously introducing chlorine into the emulsion within that zone;
   (c) continuously withdrawing emulsion from the reaction zone and causing it to flow through a cooling zone to keep its temperature between −20° and +60° C., the rate of flow of the emulsion being sufficiently high to avoid separation of the emulsion into two layers;
   (d) dividing the cooling zone effluent into major and minor portions and cycling the major portion to the inlet of the reaction zone and inlet of the cooling zone, said major portion being 4/6 to 5/6 of the cooling zone eluent, the rate of flow of the emulsion being sufficiently high to avoid the separation of emulsion into two layers;
   (e) passing a continuous stream of the minor portion of the emulsion into a first separation zone where aqueous hydrochloric acid solution is separated from a layer of alkane sulphonyl chloride; and
   (f) passing a continuous stream of the aqueous hydrochloric acid solution from said first separation zone into a second separation zone kept under reduced pressure;
   (g) recovering the layers of alkane sulphonyl chloride deposited in the first and second separation zones; and
   (h) recycling a fraction of the acid solution to the emulsifying step (a).

2. Process according to claim 1, wherein the droplets of the emulsion have diameters in the range of 0.1 to 20 microns.

3. Process according to claim 2, wherein a surface active amount of a surfactant is added to the materials subjected to said emulsifying.

4. Process according to claim 1, in which the temperature of the emulsion in the reaction zone is kept in the range of 0° to 20° C.

5. Process according to claim 4, in which the temperature is of 5° to 10° C.

6. Process according to claim 1, in which the amount of water used in the emulsification of aqueous hydrochloric acid with dialkyl disulfide is 4.4 to 12 moles $H_2O$ per mole of the disulfide.

7. Process according to claim 1, in which the concentration in HCl of the aqueous hydrochloric acid in the reaction zone is 10 to 45% by weight.

8. Process according to claim 7, wherein the concentration of HCl is 25 to 37% by weight.

9. Process according to claim 1, wherein the dialkyl disulfide is dimethyl disulfide and the product obtained is methane sulfonyl chloride.

10. Process according to claim 4, wherein the dialkyl disulfide is dimethyl disulfide and the product obtained is methane sulfonyl chloride.

11. Process according to claim 6, wherein the dialkyl disulfide is dimethyl disulfide and the product obtained is methane sulfonyl chloride.

12. Process according to claim 1, wherein vapors emitted by the acid solution in said second separation zone are passed into a scrubber and the HCl aqueous solution thus obtained is recovered.

13. Process according to claim 12, wherein the acid solution produced in the second separation zone has about 25 to 35% HCl by weight.

14. Process according to claim 1, wherein the second separation zone pressure is 10 to 500 millibars.

15. Process according to claim 1 in which a part of the fraction of acid solution in step (h) is cycled to the inlet of the cooling zone.

* * * * *